(12) United States Patent
Lieberson et al.

(10) Patent No.: US 9,956,108 B2
(45) Date of Patent: May 1, 2018

(54) SOCK ASSEMBLY FOR CORRECTING TOE DEFORMATION

(75) Inventors: Shmuel Lieberson, Haifa (IL); Aharon Liberson, legal representative, Haifa (IL); Anton Uskov, Haifa (IL); Eugeny Liberson, Haifa (IL)

(73) Assignee: TOEFIX LTD., Haifa (IL)

( * ) Notice: Subject to any disclaimer, the term of this patent is extended or adjusted under 35 U.S.C. 154(b) by 393 days.

(21) Appl. No.: 13/991,426

(22) PCT Filed: Dec. 7, 2011
(Under 37 CFR 1.47)

(86) PCT No.: PCT/IL2011/050044
§ 371 (c)(1),
(2), (4) Date: Jun. 4, 2013

(87) PCT Pub. No.: WO2012/077112
PCT Pub. Date: Jun. 14, 2012

(65) Prior Publication Data
US 2013/0261525 A1    Oct. 3, 2013

Related U.S. Application Data

(60) Provisional application No. 61/420,787, filed on Dec. 8, 2010.

(51) Int. Cl.
*A61F 5/00* (2006.01)
*A61F 5/01* (2006.01)
(52) U.S. Cl.
CPC .................................... *A61F 5/019* (2013.01)
(58) Field of Classification Search
CPC ........ A61F 5/01; A61F 5/0102; A61F 5/0104; A61F 5/0118; A61F 5/0127; A61F 5/013; A61F 5/019; A42B 7/26; A42B 17/16

USPC ........................................................... 602/30
See application file for complete search history.

(56) References Cited

U.S. PATENT DOCUMENTS

| | | | | |
|---|---|---|---|---|
| 1,785,185 A | * | 12/1930 | Day | .................................. 602/30 |
| 1,899,092 A | * | 2/1933 | Hogan | ..................... A61F 5/019 |
| | | | | 602/30 |
| 2,596,038 A | * | 5/1952 | Mayer | .............................. 602/30 |
| 2,792,001 A | * | 5/1957 | Ryan | .............................. 128/893 |
| 3,049,120 A | * | 8/1962 | Marcus | ........................... 602/30 |
| 3,063,446 A | * | 11/1962 | Levitt | ..................... A61F 5/019 |
| | | | | 602/30 |
| 3,556,091 A | * | 1/1971 | Haig | ................................ 602/30 |
| 4,414,964 A | * | 11/1983 | Farino et al. | ................... 602/30 |
| 4,632,103 A | * | 12/1986 | Fabricant et al. | .............. 602/30 |
| 4,637,381 A | * | 1/1987 | Jungmann | ....................... 602/30 |
| 4,940,046 A | * | 7/1990 | Jacoby | ............................ 602/30 |
| 5,092,347 A | * | 3/1992 | Shaffer | ................. A61F 13/064 |
| | | | | 128/892 |

(Continued)

FOREIGN PATENT DOCUMENTS

| | | |
|---|---|---|
| GB | 345590 | 3/1931 |
| WO | 2008/102405 | 8/2008 |

*Primary Examiner* — Kim M Lewis
(74) *Attorney, Agent, or Firm* — Soroker Agmon Nordman

(57) ABSTRACT

A sock assembly for correcting a deformed toe of a foot of a person, including a sock wearable on an at least a part of the foot, a strap connected to the sock and wearable on an at least a part of the foot and wrappable on an at least a part of the deformed toe as the sock it worn on the foot, consequently applying a corrective force on the deformed toe.

20 Claims, 8 Drawing Sheets

(56) References Cited

U.S. PATENT DOCUMENTS

| | | | | |
|---|---|---|---|---|
| 5,183,060 A * | 2/1993 | Shito | ............................... | 128/882 |
| 5,282,782 A * | 2/1994 | Kasahara | ......................... | 602/30 |
| 5,437,616 A * | 8/1995 | Kasahara | ......................... | 602/30 |
| 5,772,621 A * | 6/1998 | Unruh | ............................. | 602/30 |
| 2004/0215121 A1* | 10/2004 | Parker | ..................... | A61F 5/019 |
| | | | | 602/23 |
| 2010/0087766 A1* | 4/2010 | Goodes | .................. | A61F 5/019 |
| | | | | 602/30 |
| 2010/0106110 A1* | 4/2010 | De Luca | ................. | A61F 5/019 |
| | | | | 604/293 |

* cited by examiner

SOCK ASSEMBLY FOR CORRECTING TOE DEFORMATION

RELATED APPLICATIONS

The present application claims priority of a U.S. Provisional application Ser. No. 61/420,787 filed on Dec. 8, 2010.

FIELD OF THE DISCLOSURE

The present disclosure generally relate to a corrective sock assembly, and more specifically to a restrictive strap.

BACKGROUND OF THE DISCLOSURE

Hammertoe is often defined as a deformity of the toe, where the proximal interphalangeal joint of the second, third, or fourth toe causes the toe to become permanently bent, resembling a hammer. Mallet toe is a similar condition affecting the distal interphalangeal joint. Claw toe is another similar condition, in which the toe is bent in a shape resembling a predator's claw.

These conditions, jointly referred to as deformities of the toe, frequently result from muscle imbalance aggravated by wearing poorly-fit shoes. Such shoes, having excessively high heels or being too short or narrow for the foot, may force the toe into a bent position. Having the toes bent for long periods of time can cause the muscles to shorten, resulting in one of the deformity types mentioned above. This condition is often found in conjunction with bunions, calluses or other foot problems. Toe deformities can also be caused by muscle, nerve, or joint damage, resulting from conditions such as osteoarthritis, rheumatoid arthritis, stroke, Charcot-Marie-Tooth disease or diabetes. In certain age groups, the claw toe is present in every other woman. It can also be found in Friedrich's ataxia and several other neuropathies.

The main problem characterizing these conditions is usually the insufficient length of soft tissues, which constricts the toe, bends the joint, and forms a deformity (commonly a Z-deformity) of the ray. As a result, there is often dorsal prominence of the PIPJ (Proximal Interphalangeal Joint) as well as plantar prominence of the MPJ (Metatarsophalangeal Joint), the proximal phalanx, the distal metatarsal bone and the middle or distal phalanx. Those result in callosities, pain and difficulty in wearing footwear. Hallux Rigidus (also referred to as Hallux Limitus) may develop in the big toe, bringing about pain during the push-off phase of walking, discomfort and increased pressure when wearing footwear.

There are a number of known methods for treating such toe deformities. One method is padding. Different types of shoe orthotics and socks may be used to pad and cover the prominent bones, thus relieving the pressure and reducing the pain, the discomfort and further damage. Another method is based on lengthening of the soft tissues, which is achieved by physiotherapy on early stages, or surgically on late and severe stages. A further method is based on surgical shortening of bones (osteotomy, joint excision, Du Vries procedure etc.).

Many orthotics, such as insoles, are built to function as cushions which relieve the pressure under the metatarsals (metatarsal pad or metatarsal bar). Insoles are usually made of a semi-rigid, non-washable material, while a much less common version is a rigid, washable insole. The rigid ones are said to be less comfortable, and are often made of materials ranging from aluminum to plastics. During walking, the foot moves relatively to the insole, and, therefore the insole has to be custom-made, for example by casting the foot in alabaster or low-temperature thermoplastic polymer. The elevated areas have to include a relatively large surface area to adapt to the foot's motion.

Additionally, some orthotics include separate toe compartments, thus acting like a toe splint, but not to the entire ray. These orthotics do not usually have therapeutic padding under the metatarsal heads, the ray length is not adjustable, and there is a hygiene problem due to sweating of the feet. In specific orthotics which have the upper part of the toe covered by a polymer part, there is risk of callus formation; in the uncovered version, there are no restraints limiting toe bending.

Hallux Rigidus is usually treated with rigid or semi-rigid insoles, that prevent flexion of MPJ ("Morton's extension"), as well as with high shoes containing an anterior rocker. However, this form of treatment limits the patient to one pair of shoes. Another currently accepted method of treating Hallux Rigidus is surgical procedures such as MP1 fusion, MP1 implants and/or Cheilectomy. These procedures are usually expensive, painful and require a post-operative rehabilitation period.

U.S. Pat. No. 4,263,902 to Dieterich discloses an orthopedic sandal for correction of hammer-toes and X-toe (Halux Valgus) being a dual lever arm arrangement pivotable on a horizontal axis transverse to the sole. A pressure element for pressing the toes downward is on one arm and the other arm is fastened to the rearward portion of the foot so that as the food is lifted, the pressure element is pressed downwardly on the hammer-toes.

U.S. Pat. No. 6,093,163 to Chong discloses a unitary device for the correction of hallux valgus, which is made of an elastomeric fabric material that includes a large portion that encloses the forefoot circumferentially, and a smaller portion that encloses the great toe circumferentially. The fabric for constructing the device is cut in such a way that there is a bias towards varus of the great toe. Once the device is applied on the great toe and forefoot, the bias of the cut exerts a varus force on the great toe, thus correcting the valgus deformity.

U.S. Patent Application Publication No. 2008/255490 to Raija discloses a therapeutic device and method for its use. The appliance and method are adapted to realign and straighten the toes of the foot in order to treat the effects of hammertoe, bunions, Morton's neuroma, and the like. Effectively, a harness is placed about the heel of the foot, the harness consisting of a foot strap and heel strap. Sleeves are placed about the particular toes of interest, being as few as one and as many as all of the toes on a foot. Elastic straps are interconnected between the toe sleeves and the foot strap in order to impart a force to the associated toe to straighten and/or realign the toe consistent with correcting a particular malady. The elastic strap may be connected and disconnected by means of hook and loop fasteners at the end of the strap and maintained upon the toe sleeves and foot strap. The positioning of the strap with respect to the toe sleeve and the foot strap effects the direction of the force applied to the toe in accordance with the malady to be treated. Using sleeves may limit usage during rest where no active force is exerted besides the elastic forces within the straps.

The foregoing examples of the related art are intended to be illustrative and not exclusive.

SUMMARY

One exemplary embodiment of the disclosed subject matter is a sock assembly for correcting a deformed toe of a foot of a person, comprising a sock wearable on an at least a part of the foot, a strap connected to the sock and wearable on an at least a part of the foot and wrappable on an at least a part of the deformed toe as the sock it worn on the foot, consequently applying a corrective force on the deformed toe.

For clarity and without limiting, in the present disclosure the following terms are characterized as:

"Clawtoe"—A lesser toe with dorsiflexion of the proximal phalanx on the lesser metatarsophalangeal (MTP) joint and concurrent flexion of the proximal interphalangeal (PIP) and distal interphalangeal (DIP) joints.

"Enthesis"—site of attachment of a tendon to the bone.

"Gait cycle"—the entire array of movements during one step.

"Hallux Rigidus (Limitus)"—Arthropathy of the big toe, impairing dorsiflexion of the toe.

"Interphalangeal"—situated between phalanxes.

"Kissing toe osteophytes"—osteophytes appearing between the adjacent toes, usually over the joint part.

"Lumbrical muscles"—Four small skeletal muscles, numbered from the medial side of the foot, and arising from and accessory to the tendons of the flexor digitorum longus as far back as the angles of division thereof, each springing from two tendons except the first. The muscles end in tendons, which pass forward on the medial sides of the four lesser toes, and are inserted into the expansions of the tendons of the extensor digitorum longus on the dorsal surfaces of the first phalanges. All four lumbrical muscles insert into extensor hoods of the phalanges, thus creating extension at the inter-phalangeal joints.

"Prominent parts"—parts protruding beyond the overall outline of the structure referred to such as the foot.

"Osteotomy"—A surgical procedure whereby a bone is cut to shorten, lengthen, or change its alignment.

"Osteophyte" (also "bone spur")—a protruding bony formation, usually situated close to a joint or tendon attachment point.

"Ray"—the metatarsal bone, MPJ and the toe.

"Ray length"—a length measured from the proximal end of the metatarsal bone to the distal end of the toe.

"SST (subluxation second toe), underriding/overriding toe"—a common complaint among patients as pain in the second metatarsophalangeal (MTP) joint. Inflammation at this joint can result in instability, ultimately leading to $2^{nd}$ MTP joint instability (crossover toe), where the second toe crosses either under or over the adjacent toe or metatarsal bone.

"Tuber Calcanei"—the rear part of the calcaneus bone (the heel), the largest bone in the human foot.

"Tendo-Achilles"—The Achilles is the tendonous extension of two muscles in the lower leg: gastrocnemius and soleus, where in humans the tendon passes behind the ankle beginning near the middle of the calf and receives fleshy fibers on the anterior surface thereof.

"Z deformity"—a Z-shaped deformity of a toe resulting from soft tissue shortening which brings the toe into a bent position.

In the context of the present disclosure, without limiting, a 'foot' implies a human foot with members such as toes, heel, rays, etc., and referring to a person implies the human having the foot. For brevity and clarity and without limiting, in the present disclosure, the person is assumed to be a male.

In the context of the present disclosure, without limiting, referring to aspects of a foot, such as 'top', 'bottom', 'rear', 'front', 'posterior', etc. are with respect to a standing person. For example, a top view is from the head downwards. Likewise, 'proximal' and 'distal' refer, respectively, to 'close' to and 'away' from the heel.

In the context of the present disclosure, without limiting, referring to 'correcting' as with respect to a deformed toe or ray condition implies at least improving if not fully repairing the condition, and likewise, referring to 'corrective' or a variation thereof implies acting or employed for repairing the condition.

BRIEF DESCRIPTION OF THE FIGURES

Some non-limiting exemplary embodiments or features of the disclosed subject matter are illustrated in the following drawings.

Identical or duplicate or equivalent or similar structures, elements, or parts that appear in one or more drawings are generally labeled with the same reference numeral.

Figure 1:
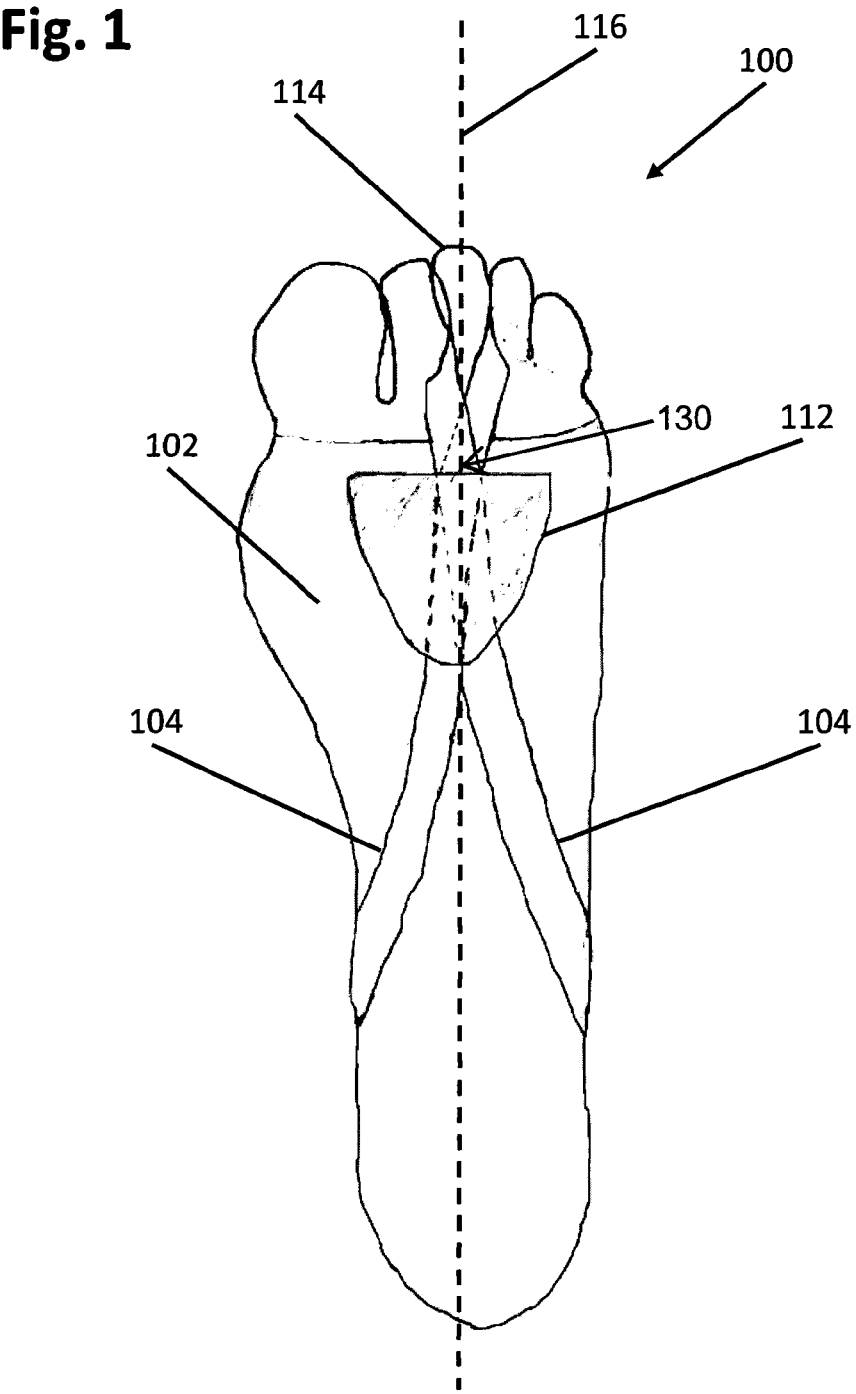

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

References to previously presented elements are implied without necessarily further citing the drawing or description in which they appear.

Figure 2:
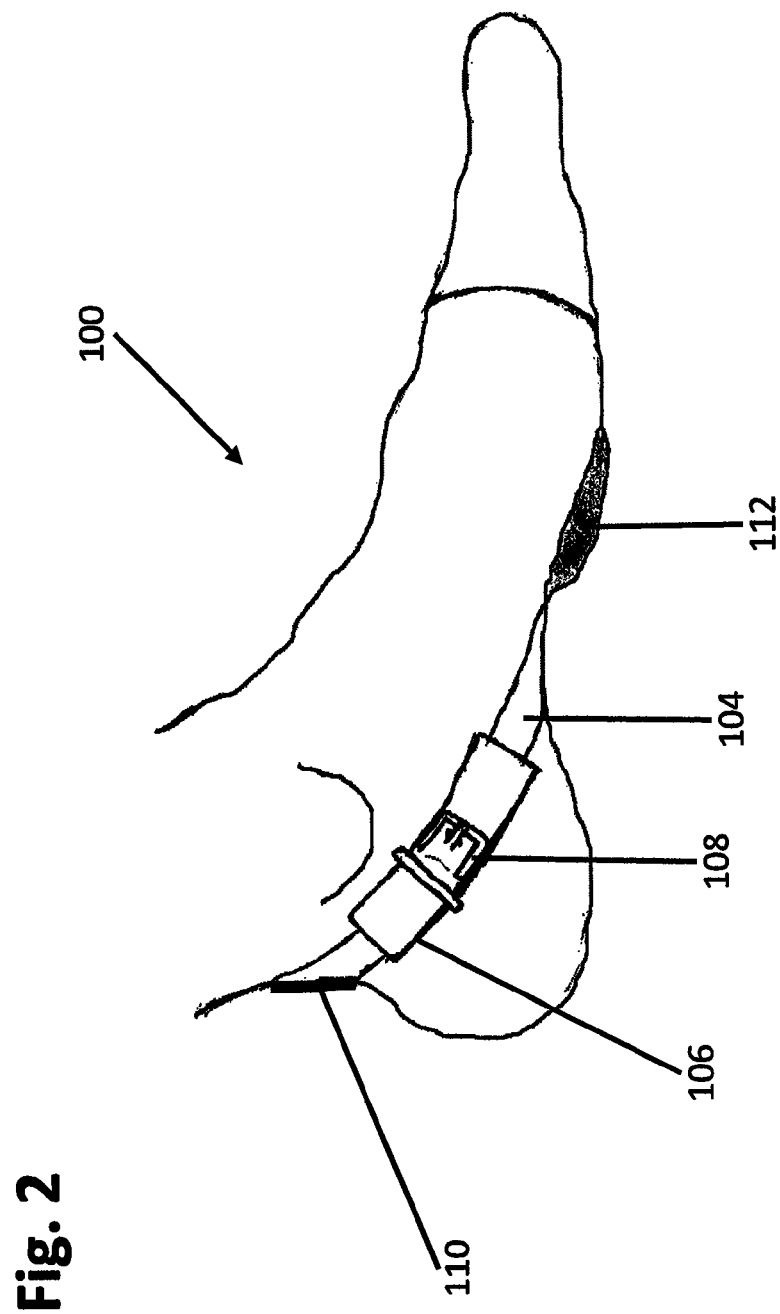
Figure 3:
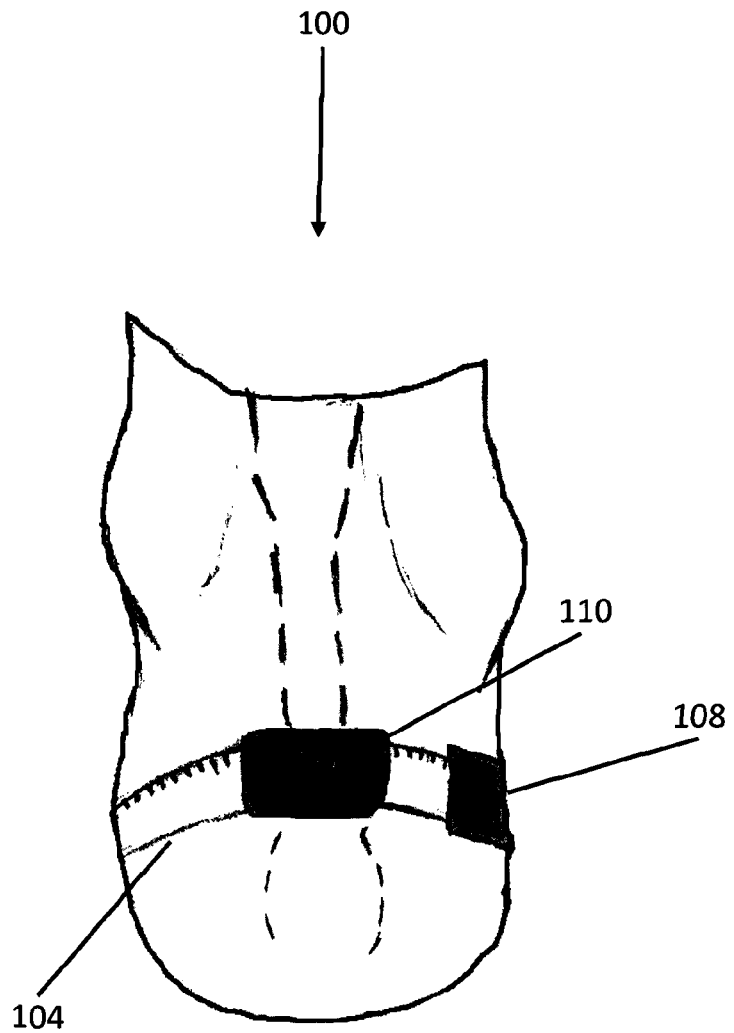
Figure 4:
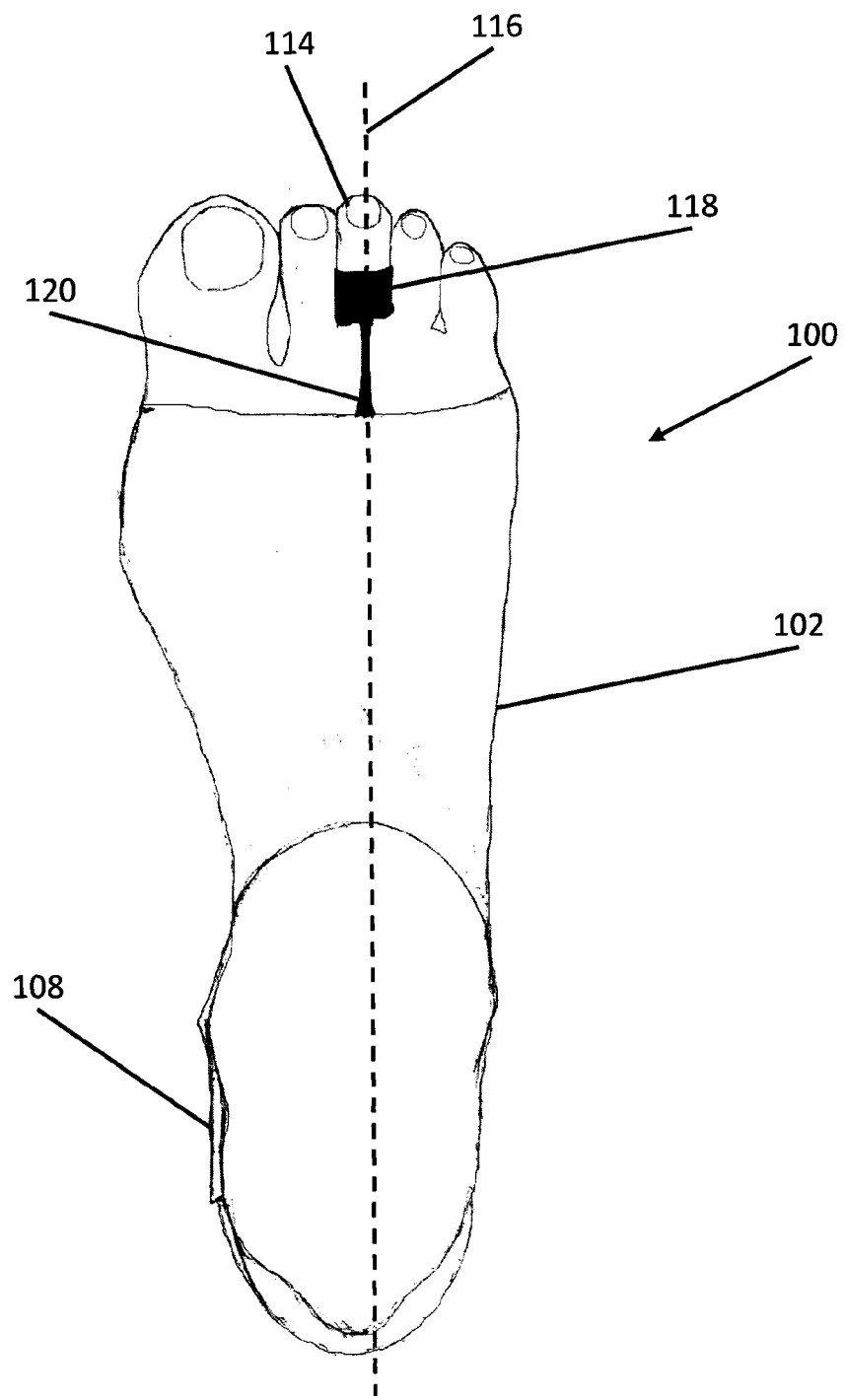
Figure 5:
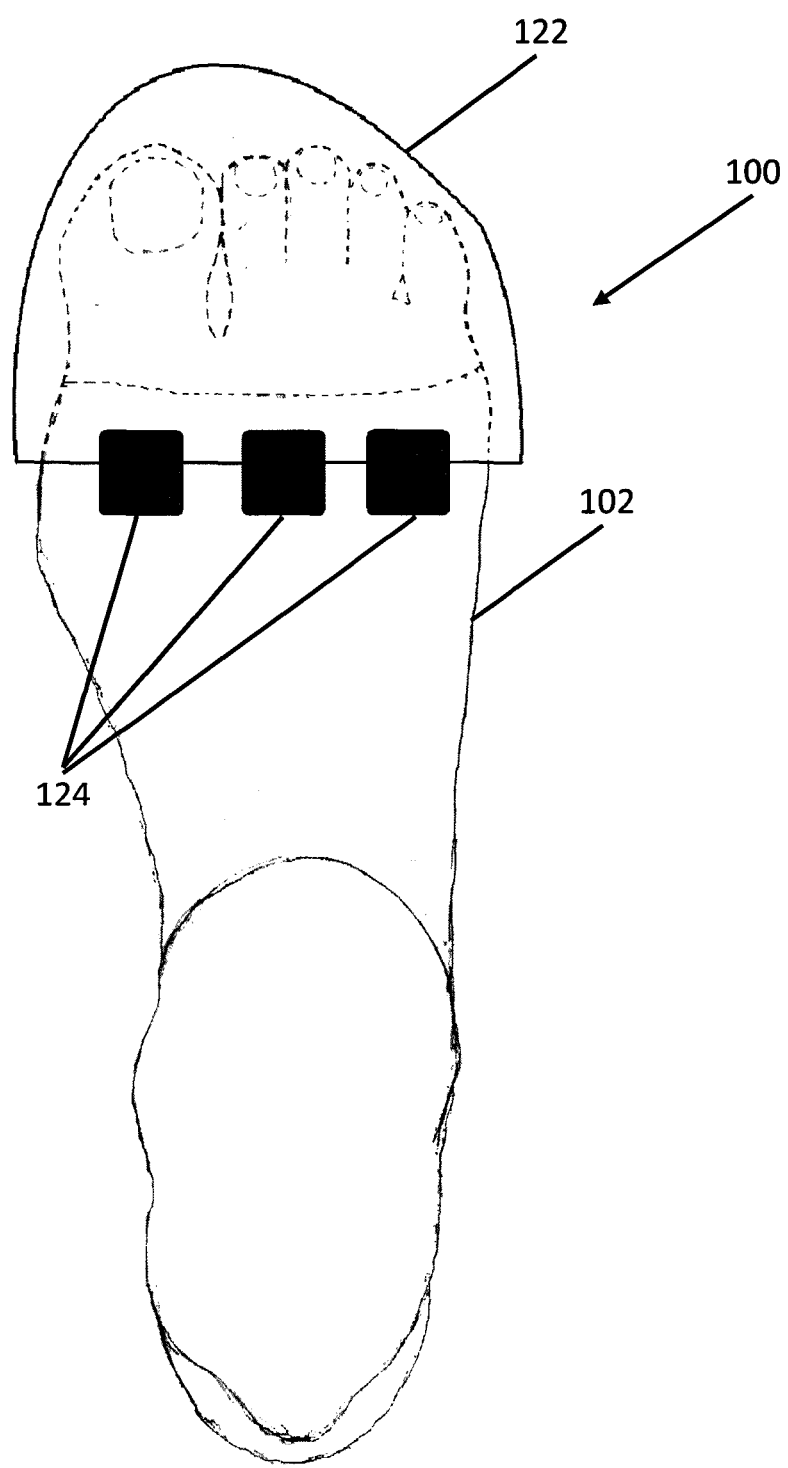
Figure 6:
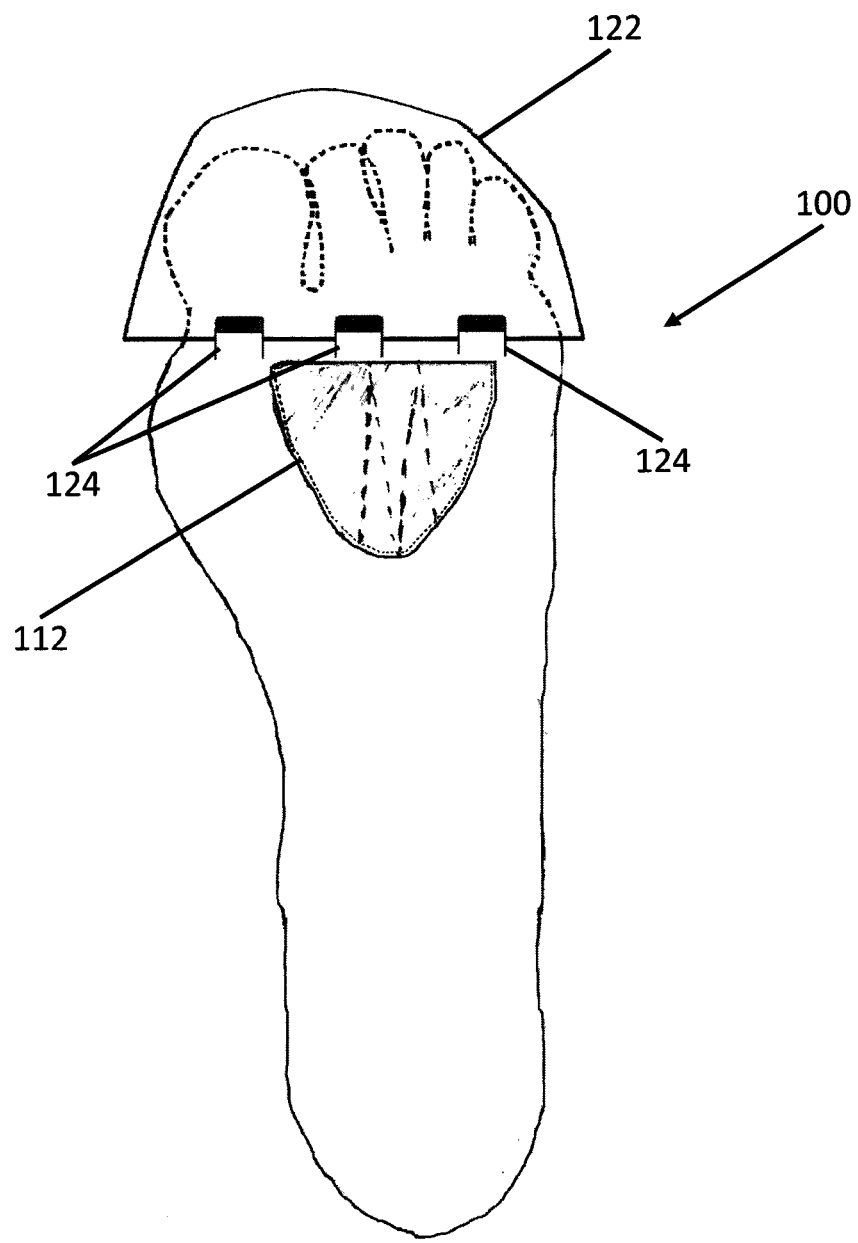
Figure 7:
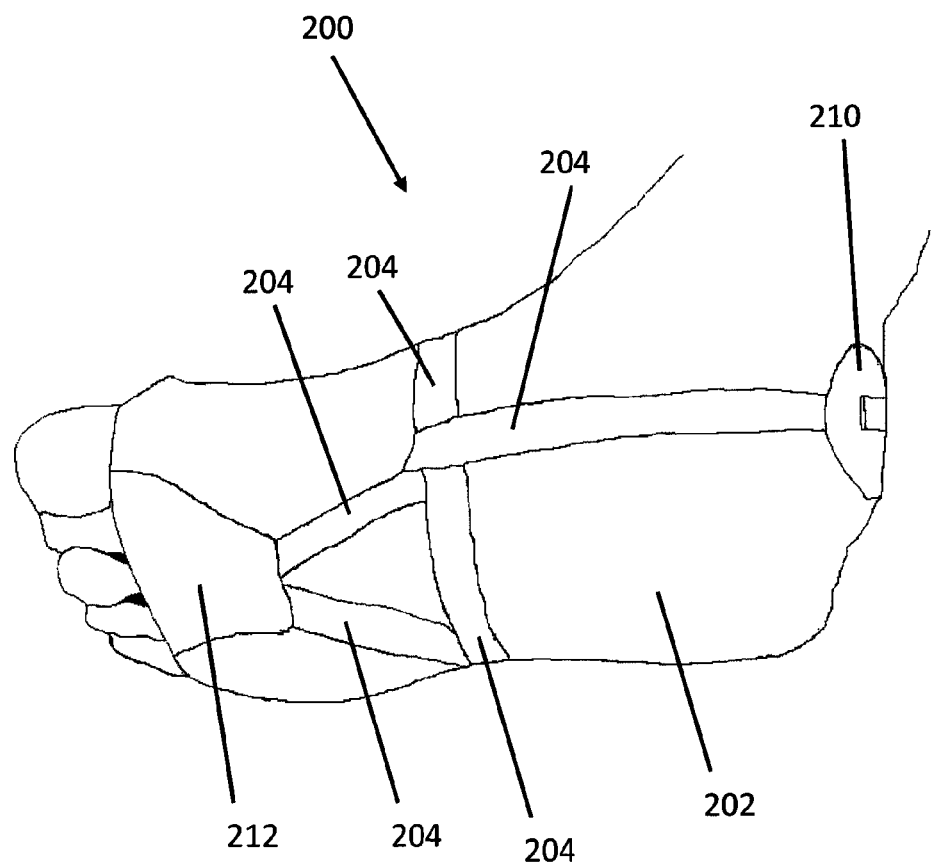
Figure 8:
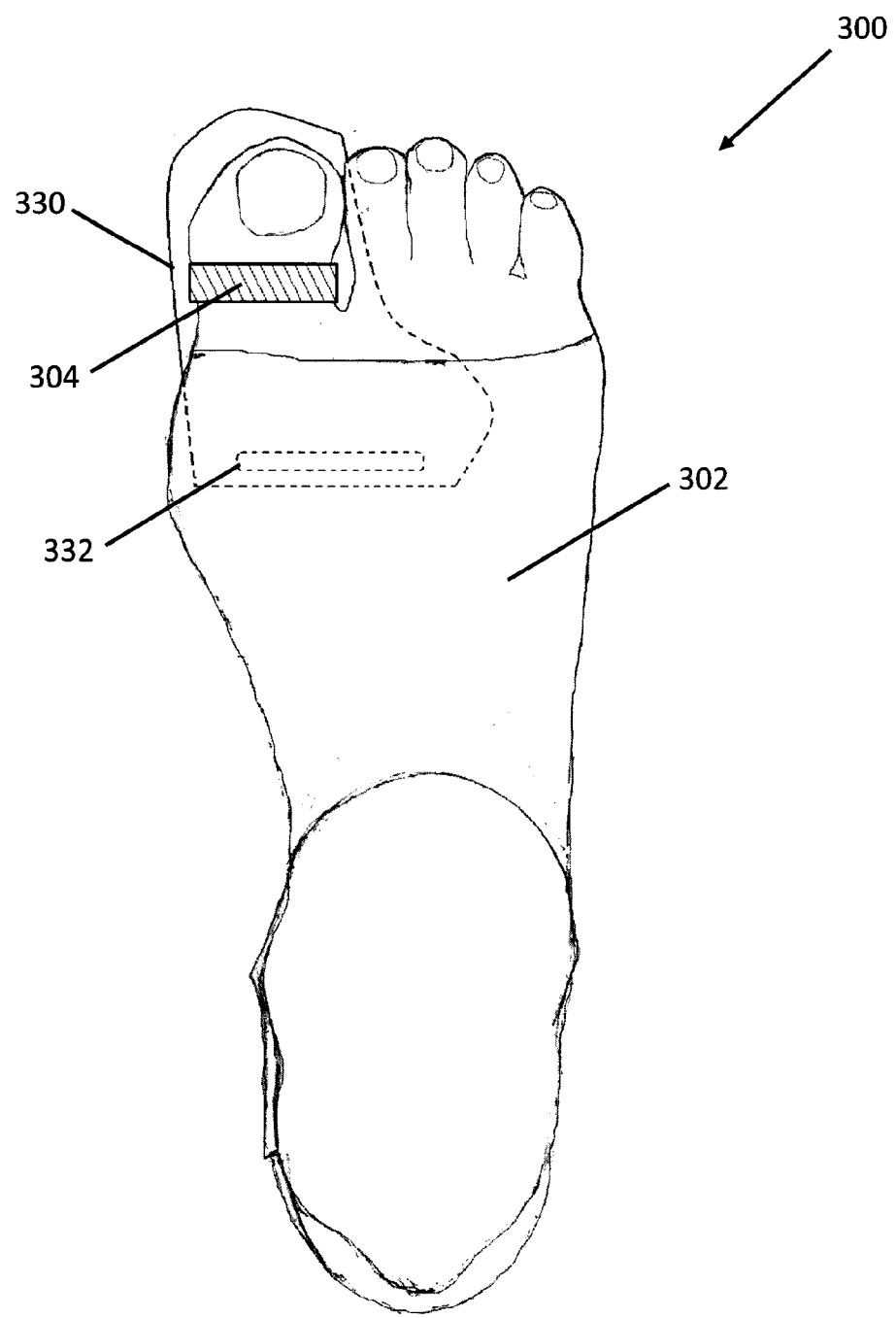

FIG. 1 schematically shows a bottom view of a corrective sock assembly, according to exemplary embodiments of the disclosed subject matter;

FIG. 2 schematically shows a side view of the corrective sock assembly, according to exemplary embodiments of the disclosed subject matter;

FIG. 3 schematically shows a rear view of the corrective sock assembly, according to exemplary embodiments of the disclosed subject matter;

FIG. 4 schematically shows a top view of the corrective sock assembly, according to exemplary embodiments of the disclosed subject matter;

FIG. 5 schematically shows a top view of a corrective sock assembly including a toe protector, according to exemplary embodiments of the disclosed subject matter;

FIG. 6 schematically shows a top view of the corrective sock assembly including the toe protector, according to exemplary embodiments of the disclosed subject matter;

FIG. 7 schematically shows a lower perspective view of a corrective sock assembly having its restrictive strap secured to the foot from multiple directions, according to exemplary embodiments of the disclosed subject matter; and FIG. 8 schematically shows a top view of a corrective sock assembly including a rigid protection plate limiting dorsiflexion of the Hallux, according to exemplary embodiments of the disclosed subject matter.

DETAILED DESCRIPTION

One technical problem dealt by the disclosed subject matter is correcting a deformation of a toe.

One technical solution according to the disclosed subject matter is a sock assembly, including a sock disposed on the foot or part thereof and comprising or connecting with a strap wrapped around a toe and/or a respective ray or part thereof, thereby applying a force on the toe or respective ray, yielding a non-invasive, repetitive and gradual correction of a toe deformation such as hammertoe, claw toe and/or a similar condition or conditions.

The sock as an assembly or combination of a sock with a strap enables to put the sock on the foot along with the strap whereby the strap is guided to a target toe or ray for applying a corrective force, and further provides for maintaining the position of the strap when the foot moves such as in walking, optionally further maintaining the position of other elements such as pads.

A potential technical effect of the disclosed subject matter is a self-positioning of a strap for correcting a deformation of a toe.

In some embodiments, the restrictive strap is configured for repairing a toe deformation by mimicking the function of intrinsic muscles, gradually correcting the deformity of the toe during daily activities. The restrictive strap is placed under the affected ray, and the correction is achieved, at least partially, by elongation of soft tissues relative to the bony structures of the foot so that, in some embodiments, the force exerted by body weight in the direction of a lumbrical muscle would gradually straighten the toe during walking.

In some embodiments, the restrictive strap is attached to the sock in one or more areas for proper fit and ease of use, such that it would be disposed over the heel and/or over the affected ray. The restrictive strap is attached to the sock by, for example, stitches, hooks, hooks-and-loops or an adhesive.

Additionally, in some embodiments, the corrective sock assembly includes a toe protector device, situated over the frontal part of the foot which is not covered by the sock, for protective and/or cosmetic purposes.

In some embodiments, the corrective sock assembly introduces painless, or somewhat painful, force on the toe, wherein the force is optionally changeable such as by gradual adjustment of the strap length and/or elasticity.

The treatment schedule and tension applied to the restrictive strap may be controlled by the person on a daily basis.

The corrective sock assembly is designed for easy handling, as self-usage by the person, and may be used as an effective preventive measure, at least to a certain degree, for persons prone to toe deformity formation.

Generally, the corrective sock assembly does not require custom-made manufacturing to achieve proper fit, and can be simply chosen according to person foot size. In some embodiments, the corrective sock assembly is made of fabric, optionally with some other constituents, and may be manufactured by contemporary textile technology, so that the corrective sock assembly is foldable and washable as or similar to a conventional cloth, thereby reducing wear-out and/or improving hygiene relative to non-washable socks. In some embodiments, the sock per se is made of fabric whereas the other parts, such as straps or pads (discussed below) are not necessarily made of fabric.

The entire corrective sock assembly is configured for easy and convenient wearing, and incorporation in a sock that covers part of or the entirety of the foot provides a sufficient or acceptable aesthetic appearance.

In some embodiments, the corrective sock assembly is sufficiently thin to be worn inside footwear.

In some embodiments, the corrective sock assembly includes one or more pads made of a shock absorbing material, such as silicone or a foamed polymer, and positioned under the heel and/or under the metatarsal base and/or under any other prominent part. Having a pad in the corrective sock assembly under the metatarsal base may, in some embodiments, replace tailor-made orthotics.

In some embodiments, the pad or pads are adhered to the corrective sock assembly so that movement a pad in the corrective sock assembly is restricted. Thus, a pad may be smaller compared to an insole-based padding since there is less freedom of motion of the foot in relation to the sock.

In some embodiments or circumstances, the corrective sock assembly may also be used before and/or after and/or instead of surgical treatment, especially in cases of SST (subluxation second toe).

In some embodiments, the corrective sock assembly comprises a plurality of straps, and in some embodiments, a sock is not necessarily a full sock but, rather, a partial sock such as half-sock.

The description below, without limiting, refers by way of example to a deformed toe and/or ray.

Reference is now made to FIG. 1, which schematically shows a corrective sock assembly 100 from a bottom view, according to exemplary embodiments of the disclosed subject matter, and a toe 114 lying along an axis 116 of an affected ray 130. Reference is further made to FIG. 2 which schematically shows corrective sock assembly 100 from a side view, and to FIG. 3 which schematically shows corrective sock assembly 100 from a rear view, according to exemplary embodiments of the disclosed subject matter.

Corrective sock assembly 100 includes a sock 102 and a restrictive strap 104 which is wrapped over the top part of toe 114, and under a proximal part of affected ray 130. Restrictive strap 104 may be safely and comfortably anchored attached to an Achilles pad 110 made of a soft material and positioned over the heel bump (also "Tuber Calcanei") in a way that protects the tender Tendo Achilles enthesis area from direct contact with the strap. Securing of restrictive strap 104 utilizes a reaction force generated upon movement of the foot, such as when walking or running, for exertion a straightening force on the toe, creating repetitive, gradual elongation of soft tissues of affected ray 130.

Optionally, restrictive strap 104 may be crossed in an area following the wrapping of toe 114 under the metatarsal area, and opening again on two sides of the foot towards the Achilles tendon.

In some embodiments, restrictive strap 104 is positioned, at least partly, inside sock 102, such that restrictive strap 104 is minimally or partially visible from outside of sock 102. Optionally, the frontal part of sock 102 includes suitable slits through which restrictive strap 104 is threaded in and out of sock 102.

Corrective sock assembly 100 may be placed anew every day on the foot, applying a tension such as to prevent pain or allow certain pain. Optionally the tension is increased relative to previous positioning of corrective sock assembly 100, providing a gradual elongation of the soft tissues.

In some embodiments, restrictive strap 104 is elastic, providing stretching or elastic force on toe 114. Optionally or alternatively, restrictive strap 104 is inelastic, providing a pulling force on toe 114. Optionally, restrictive strap 104 is elastic in a part thereof and inelastic in another part, for example, inelastic in a part that is wrapped around toe 114 and elastic in a part wraps around the foot to provide a firm positioning. In some embodiments, restrictive strap 104 is of controlled or limited elasticity, such as by elastic threads interwoven with non-elastic material.

In some embodiments, restrictive strap 104 is modular, enabling individual application to a plurality of rays or toes, optionally including all five rays or toes. For example, restrictive strap 104 comprises a plurality of straps, or, for example, restrictive strap 104 is splitted to sub-strips for individual rays or toes. In some embodiments, restrictive strap 104 comprises, or formed as, one or more bands that wraps or wrap a plurality of rays or toes, thereby applying corrective force simultaneously on a plurality of rays or toes.

In some embodiments, in order to provide a proper or sufficient fit on the foot and ease of use in wearing on the foot, restrictive strap 104 is attached to or connects to sock 102 over the heel and/or over affected ray 130, for example, by stitches, hooks, an adhesive, threaded through one or more apertures in the sock, or any other means such as hooks-and-loops.

In some embodiments, a metatarsal pad 112 is placed at the bottom of sock 102 beneath the foot's metatarsal pad or base. In order to accommodate metatarsal pad 112 and position thereof in a suitable place, restrictive strap 104 is treaded through metatarsal pad 112, or restrictive strap 104 is placed between sock 102 and metatarsal pad 112. Optionally, other manners are used for placing metatarsal pad 112 at suitable place, such as an adhesive.

In some embodiments, metatarsal pad 112 comprises or made of a soft material, such as silicone or foamed material such as polystyrene foam.

In some embodiments, metatarsal pad 112 creates a pivot that enables restrictive strap 104 to straighten affected ray 130 by mimicking or simulating or affecting a pull in the direction of intrinsic muscles' pull and utilizing the person's weight load as a source of corrective force. Since metatarsal pad 112 elevates one or more of the person's metatarsals, and restrictive strap 104 pulls down the affected toe, the intrinsic muscles are stretched and affected ray 130 deformation is straightened at least to some extent. Thus, metatarsal pad 112 complements and enhances the straightening force exerted by the restrictive strap.

In some embodiments, a fastener, represented without limiting as a buckle 108, is used to adjust the length of restrictive strap 104, and in some embodiments, a buckle pad 106 is attached to buckle 108 or at a respective position thereof on sock 102, providing comfort cushioning beneath buckle 108.

Reference is now made to FIG. 4, which schematically shows corrective sock assembly 100 from a top view, according to exemplary embodiments of the disclosed subject matter.

In some embodiments, a toe pad 118 is placed over the IPJ (interphalangeal joint) of toe 114 and connected to restrictive strap 104 and to sock 102 using a bridge 120. In some embodiments, bridge 120 comprises or made of a wire, an elongated piece of fabric or other apparatus such as an elongated piece of plastic or metal.

In some embodiments, toe pad 118 placed on or at least partly around toe 114 is configured to mitigate pain resulting from a shoe pressing on the toe, which is generally known with conditions such as hammertoe, claw toe, mallet toe and the like.

In some embodiments, a separating pad, such as toe pad 118 or a modified form thereof, is placed at least partly on a toe and/or two neighboring toes where the separating pad separates between the neighboring toes. In cases such as neighboring deformed toes or sore toes that may or do press against each other and cause discomfort or inflict pain, the separating pad detaches the toes from each other and/or provides cushioning to ease the discomfort and/or pain.

Reference is now made to FIG. 5 and FIG. 6, which shows corrective sock assembly 100 from a top and a bottom view, respectively, a according to exemplary embodiments of the disclosed subject matter.

In some embodiments, a toe protector cup 122 covers the frontal part of corrective sock assembly 100, where, optionally, toe protector cup 122 have one or more cuts through which the restrictive strap 104 is optionally inserted.

In some embodiments, toe protector cup 122 is formed from a rigid material or a soft fabric or other material and is configured to enclose and protect the foot front. Optionally, toe protector cup 122 is detachably connected to sock 102 by one or more of a toe protector strap 124 used to attach toe protector cup 122 to the front of sock 102. Optionally or alternatively, toe protector cup 122 is integrally formed with sock 102.

In some embodiments, corrective sock assembly 100 includes one or more additional pads, optionally made from a soft material, and placed over the protruding, prominent parts and/or pressure points of the foot to prevent pressure or friction thereon.

In some embodiments, sock 102 covers also the frontal part of the foot, and optionally includes separate compartments for each of the toes. In such a case as described, restrictive strap 104 may be wrapped around the affected toe or toes externally to sock 102.

Reference is now made to FIG. 7, which shows another corrective sock assembly 200 from a lower perspective view, a according to exemplary embodiments of the disclosed subject matter. Similar to corrective sock assembly 100, corrective sock assembly 200 includes a sock 202 and a restrictive strap 204. In some embodiments, corrective sock assembly 200 includes a metatarsal pad 212 akin to metatarsal pad 112 and/or an Achilles pad 210 akin to Achilles pad 110.

In some embodiments, restrictive strap 204 is configured to be wrapped around the person's foot, securing restrictive strap 204 at least suitably or sufficiently to the foot from multiple directions, as illustrated by multiple instances or parts of restrictive strap 204.

Reference is now made to FIG. 8, which shows yet another corrective sock assembly 300, according to exemplary embodiments of the disclosed subject matter. In some embodiments, akin to corrective sock assembly 100, corrective sock assembly 300 includes a sock 302 and a restrictive strap 304 (illustrated partially). Corrective sock assembly 300 further include, in some embodiments, a metatarsal pad and/or an Achilles pad (both not shown).

In some embodiments, corrective sock assembly 300 is suitable, at least partially or sufficiently, for limiting hallux dorsiflexion and correcting Hallux Rigidus, by employing a rigid protection plate 330 positioned below the hallux and extending towards the metatarsals and heel. Simultaneously, in some embodiments, restrictive strap 304 pulls the hallux downwards rigid protection plate 330 and flattens the hallux onto rigid protection plate 330 and/or the sole. In some embodiments, rigid protection plate 330 is connected to corrective sock assembly 300 by permanent or detachable attachment to either one or both of sock 302 or restrictive strap 304. For example, an aperture 332 may be provided in rigid protection plate 330 through which restrictive strap 304 may be threaded. In some embodiment, rigid protection plate 330 is a part of a toe protector cup, such as toe protector cup 122.

In some embodiments, rigid protection plate 330 comprises or made of a rigid material such as metal or plastic. As used herein, the term 'rigid' with respect to an object implies an object inflexible and/or unbendable and/or partly bendable while maintaining the general form thereof under forces exerted thereon by movement of the foot and/or the person's weight.

It is noted and emphasized that, at least in some embodiments, the sock assembly comprising the strap or straps enables to dress the sock assembly on the foot as a sock while concurrently placing the strap or straps in the indented position or position on the foot and toe or toes; that is, no particular handling and placing of the strap or straps is required. Likewise, at least in some embodiments, the sock provides for placing the pad or pads in the intended position or positions and no particular handling and placing of the pad or pads is required.

Further, while the sock assembly is on the foot, the sock provides for keeping the elements of the sock assembly in place when the foot moves such as in walking or running.

It is noted that correcting a deformation of a toe and/or ray is carried out by external mechanical means by a force due to the person's foot movement and/or person's weight and, therefore, does not constitute a treatment of the human body.

It is thus provided according to the present disclosure a sock assembly for correcting a deformed toe of a foot of a person, comprising a sock wearable on an at least a part of the foot, a strap connected to the sock and wearable on an at least a part of the foot and wrappable on an at least a part of the deformed toe as the sock it worn on the foot, consequently applying a corrective force on the deformed toe.

In some embodiments, the corrective force is due to, at least partially, to a movement of the foot.

In some embodiments, the sock assembly is configured to be worn while placing the strap, at least partly on the at least a part of the deformed toe.

In some embodiments, the sock assembly is configured to gradually apply the corrective force on the deformed toe.

In some embodiments, the sock is configured to sufficiently maintain the position of the strap on the foot.

In some embodiments, the strap comprises a plurality of straps.

In some embodiments, the strap is formed and configured to wrap, at least partially, on a plurality of deformed toes, thereby applying a corrective force on the plurality of toes.

In some embodiments, the deformed toe further includes an at least a part of a corresponding ray thereof.

In some embodiments, the sock assembly comprises an at least one pad placeable on the foot the as the sock it worn on the foot.

In some embodiments, the at least one pad is placed under at least one of: the heel, the metatarsal base, the deformed toe, or a prominent part of the foot.

In some embodiments, the strap connects to the at least one pad placed under the metatarsal base, thereby creating a pivot and pulling by a force due to the person's weight the corresponding ray of the deformed toe in the direction of intrinsic muscles' pull.

In some embodiments, at least one pad is placed over the heel bump and attached to the strap, thereby protecting the tender Tendo Achilles enthesis area from direct contact with the strap.

In some embodiments, the sock is configured to sufficiently maintain the position of the at least one pad on the foot.

In some embodiments, the sock assembly further comprises a rigid device positioned below the hallux and extending towards the metatarsals and heel for limiting hallux dorsiflexion and correcting Hallux Rigidus.

In some embodiments, the strap pulls the hallux downwards the rigid device and flattens the hallux onto at least one or both of the rigid device or sole.

In some embodiments, the sock assembly further comprises a protecting device for protecting at least one of deformed toe.

It is noted that the apparatus and methods described above are provided as examples and variations thereof, or other methods and apparatus for applying corrective force to a toe are not precluded from the scope of the present disclosure.

As used herein, the singular forms "a", "an" and "the" are intended to include the plural forms as well, unless the context clearly indicates otherwise. It will be further understood that the terms "comprises" and/or "comprising" and/or "having" when used in this specification, specify the presence of stated features, integers, steps, operations, elements, and/or components, but do not preclude the presence or addition of one or more other features, integers, steps, operations, elements, components, and/or groups thereof.

As used herein the term "configuring" for an objective, or a variation thereof, implies using materials and/or components in a manner designed for and/or implemented and/or operable or operative to achieve the objective.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A sock assembly (100, 200, 300) for correcting deformed toes (114) of a foot of a person, comprising:
    a sock (102, 202, 302) wearable on at least a part of the foot;
    a strap (104, 204, 304) comprising two ends, said strap connected to the sock and configured to be wearable on at least a part of the foot,
    the sock assembly characterized in that the strap is wrappable directly and independently of any other supplementary extra element on a plurality of deformed toes, at least partially, and further wherein said strap is adapted to cross itself under a foot's metatarsal area following the strap wrapping the deformed toes, said strap further adapted to extend along two sides of the foot towards the Achilles tendon of the person, which is adjacent to a location at which the two ends of the strap meet, thereby applying a corrective force on the plurality of deformed toes.

2. The sock assembly according to claim 1, wherein the corrective force is due, at least partially, to a movement of the foot in walking.

3. The sock assembly according to claim 1, wherein the sock assembly is configured to be worn while wrapping the strap, at least partly, on the plurality of deformed toes.

4. The sock assembly according to claim 1, wherein the sock assembly is configured to apply the corrective force gradually by adjustment of at least one of the strap's length or the strap's elasticity.

5. The sock assembly according to claim 1, wherein the sock is configured to sufficiently maintain the position of the strap on the foot.

6. The sock assembly according to claim 1, wherein the strap comprises a plurality of straps.

7. The sock assembly according to claim 1, wherein the strap is wrappable externally to the sock.

8. The sock assembly according to claim 1, further comprising a fastener for adjusting the length of the strap, wherein said fastener is positioned along the strap, at the location at which the two ends of the strap meet.

9. A sock assembly (100, 200, 300) for correcting deformed toes (114) of a foot of a person, comprising:
    a sock (102, 202, 302) wearable on at least a part of the foot;

a strap (104, 204, 304) comprising two ends, said strap connected to the sock and configured to be wearable on at least a part of the foot, the sock assembly characterized in that the strap is wrappable, directly and independently of any other supplementary extra element, on at least a part of at least one deformed toe as the sock is worn on the foot, and further wherein said strap is adapted to cross itself under a foot's metatarsal area following the strap wrapping the at least one deformed toe, said strap further adapted to extend along two sides of the foot towards the Achilles tendon of the person, which is adjacent to a location at which the two ends of the strap meet, consequently applying a corrective force on the deformed toe, and said sock assembly further characterized in having an at least one pad (110, 112, 118, 210, 212) placeable at the bottom of the sock beneath the foot's metatarsal area to elevate at least one metatarsal thereby complementing and enhancing the force applied by the strap.

10. The sock assembly according to claim 9, wherein the at least one pad is placeable beneath the foot as the sock worn on the foot.

11. The sock assembly according to claim 9, wherein the at least one pad is placeable under at least one of: a metatarsal head, the deformed toe, or a prominent part of the foot.

12. The sock assembly according to claim 11, wherein the strap connects to the at least one pad placed under the metatarsal head, thereby creating a pivot and pulling a ray of the deformed toe by a force due to the person's weight toe in a direction of intrinsic muscles' pull.

13. The sock assembly according to claim 9, wherein the least one pad is attached to the strap and placeable over a heel bump, thereby protecting a tender *tendo* achilles enthesis area from direct contact with the strap.

14. The sock assembly according to claim 9, wherein the sock is configured to sufficiently maintain the position of the at least one pad beneath the foot by adhering the at least one pad to the sock.

15. The sock assembly according to claim 9, further comprising a rigid protection plate (330) positioned below a hallux and extending towards metatarsals and a heel for limiting hallux dorsiflexion and correcting hallux rigidus.

16. The sock assembly according to claim 15, wherein the strap pulls the hallux downwards to the rigid protection plate and flattens the hallux onto at least one or both of the rigid device or sole.

17. The sock assembly according to claim 9, further comprising a toe protector cup (122) for rigidly protecting at least one of the deformed toes.

18. The sock assembly according to claim 9, wherein the at least one deformed toe comprises a plurality of deformed toes.

19. The sock assembly according to claim 9, wherein the at least one pad is placeable outside and apart of the sock.

20. The sock assembly according to claim 9, further comprising a fastener for adjusting the length of the strap, wherein said fastener is positioned along the strap, at the location at which the two ends of the strap meet.

* * * * *